United States Patent [19]

Wedig et al.

[11] 4,401,666

[45] Aug. 30, 1983

[54] USE OF METALLIC SALTS OF PYRIDINE-2-THIONE-N-OXIDE TO TREAT OR PREVENT BOVINE MASTITIS

[75] Inventors: John H. Wedig, Guilford, Conn.; John G. Babish, Ithaca, N.Y.; Jeffrey Davidson, Tulare, Calif.

[73] Assignee: Olin Corporation, New Haven, Conn.

[21] Appl. No.: 344,666

[22] Filed: Feb. 1, 1982

[51] Int. Cl.³ .................... A61K 31/555; A61K 31/44
[52] U.S. Cl. ..................................... 424/245; 424/263
[58] Field of Search ............................... 424/245, 263

[56] References Cited

U.S. PATENT DOCUMENTS

| | | |
|---|---|---|
| 3,636,194 | 1/1972 | Parizeau . |
| 3,753,990 | 8/1973 | Curry ................................ 424/49 |
| 4,070,469 | 1/1978 | Haber et al. . |
| 4,172,138 | 10/1979 | Rhodes . |
| 4,199,564 | 4/1980 | Silver et al. . |

OTHER PUBLICATIONS

Merck Veterinary Manual-4th Edit., (1973), pp. 808 and 809.
Fukuzumi et al.-Chem. Abst., vol. 91, (1979), p. 70002e.
Schalm et al, Bovine Mastitis, Lea & Febiger Publishers, Philadelphia, pp. 136 to 140, (1971).
Olin Corp., Literature Search #81-135.
Olin Corp., Product Brochure for Omadine® Brand Sodium and Zinc Pyridine-2-Thione-N-Oxide Products.
Cloyd et al, "Ocular Toxicity Studies with Zinc Pyridinethione", Toxicology and Applied Pharmacology, vol. 45, pp. 771-782, (1978).
Davidson et al, "Bovine Mastitis: Antimicrobial Resistance Patterns", Reprinted from the Journal of the American Veterinary Medical Association, vol. 180, No. 2, pp. 153-155, (1982).
Snyder et al, "Safety Evaluation of Zinc 2-Pyridinethiol 1-Oxide in a Shampoo Formulation", Toxicology and Applied Pharmacology, vol. 7, pp. 425-437, (1965).

*Primary Examiner*—Sam Rosen
*Attorney, Agent, or Firm*—William A. Simons; Thomas P. O'Day

[57] ABSTRACT

Described is a method for treating an animal for bovine mastitis wherein said animal is administered an effective amount of at least one metallic salt of pyridine-2-thione-N-oxide to treat or prevent bovine mastitis.

8 Claims, No Drawings

USE OF METALLIC SALTS OF PYRIDINE-2-THIONE-N-OXIDE TO TREAT OR PREVENT BOVINE MASTITIS

BACKGROUND OF THE INVENTION

1. Field of the Invention

This invention relates to the use of metallic salts of pyridine-2-thione-N-oxide to prevent or treat bovine mastitis.

2. Description of the Prior Art

Bovine mastitis is an infection of the udder of ruminants such as cows, mainly caused by gram positive bacteria and especially in cows in intensive milk producing units. It results in the inflammation of the mammary gland (i.e., teats and udder). The disease is particularly troublesome and of considerable economic importance because the pathogen is readily transferred from one animal to another during the milking process. Some of the main pathogens causing bovine mastitis are *Staphylococcus aureus, Streptococcus agalactiae, Streptococcus uberis, Streptococcus dysgalactiae, Escherichia coli, Aerobacter aerogenes, Klebsiella pneumoniae,* and *Pseudomonas aeruginosa.*

Effective compounds to be used in the treatment or prevention of bovine mastitis should give the following results:

1. Most or all of the above pathogens should be susceptible to the compound when the latter is in milk and other udder fluids.
2. The therapeutic effect should be relatively quick.
3. No significant irritation should be caused to the teats or udder of the cow, either by the active compound or other ingredients used with it.
4. The active compound should not stay in the milk for a period much in excess of the one required for the therapeutic activity so as to minimize the loss of milk, which has to be discarded as long as an undesired foreign compound is present.

There are other requirements for such a composition for the treatment of bovine mastitis but the above four criteria are some of the most important ones.

Bovine mastitis has so far been treated mainly by administering anti-microbial agents such as antibiotics, e.g. Penicillin G, Dihydrostreptomycin, and the like. However, it has been recently found to be very desirable to replace antibiotics by non-antibiotic drugs. The following are some reasons why:

1. Antibiotics effective in human medicine should not be utilized in veterinary medicine, in order not to build up a strain resistance against bacteria appearing in human diseases.
2. *Staphylococcus aureus,* one of the above-noted pathogens, has already built up a resistance against most of the antibiotics utilized in the treatment of bovine mastitis.

It has thus been very important to find a method for the treatment of bovine mastitis utilizing a non-antibiotic compound which substantially would overcome the drawbacks of antibiotics utilized so far and would give the desired results as set out above.

Separately, the anti-microbial properties of metallic salts of pyridine-2-thione-N-oxide, also known as [1-hydroxy-2(1H)pyridinethionano] salts are well known. These compounds have been employed in skin cleansing compositions and in antidandruff shampoo compositions. Another application of metallic salts of pyridine-2-thione-N-oxide is as a preservative against the growth of microorganisms in compositions, for example, cosmetic compositions.

BRIEF SUMMARY OF THE INVENTION

The present invention, therefore, is directed to treating an animal for bovine mastitis which comprises administering to said animal an effective amount of at least one metallic salt of pyridine-2-thione-N-oxide to treat or prevent bovine mastitis.

DETAILED DESCRIPTION

As stated above, metallic salts of pyridine-2-thione-N-oxide are a well-known class of compounds and are generally made by reacting a metallic salt with 2-mercaptopyridine-N-oxide. Suitable metallic salts of pyridine-2-thione-N-oxide may be alkali metal salts such as sodium and heavy metal salts such as zinc, ferric ($Fe^{+3}$), cupric ($Cu^{+2}$), and other metal salts such aluminum. Because of their commercial availability, the zinc and sodium salts of pyridine-2-thione-N-oxide are the most preferred metal salts.

The zinc salt of pyridine-2-thione-N-oxide, also known as bis[1-hydroxy-2(1H)pyridinethionato]zinc, is made by reacting a metallic salt (e.g., $ZnCl_2$ or $ZnSO_4$) with 2-mercaptopyridine-N-oxide. Exemplary methods for making this compound are disclosed in U.S. Pat. No. 2,809,971, which issued to Bernstein et al. on Oct. 15, 1957, and in U.S. Pat. No. 4,080,329, which issued to Mantwyler on Mar. 21, 1978.

The sodium salt of pyridine-2-thione-N-oxide, also known as 2-pyridinethiol-1-oxide, Na salt, is generally made by reacting a 2-halopyridine-N-oxide (e.g. 2-chloropyridine-N-oxide) with sodium hydrosulfide (NaSH) in aqueous solution under a slightly alkaline condition or with a mixture of sodium sulfide ($Na_2S$) and sodium hydrosulfide. Exemplary methods for making this compound are disclosed in U.S. Pat. No. 2,686,786, which issued to Shaw et al on Aug. 17, 1954; U.S. Pat. No. 3,159,640, which issued to McClure et al. on Dec. 1, 1964; and U.S. Pat. No. 3,892,760, which issued to Hooks et al on July 1, 1975.

Other metallic salts of pyridine-2-thione-N-oxide are disclosed in U.S. Pat. No. 3,347,863, which issued to Ottman et al on Oct 17, 1967, (aluminum); U.S. Pat No. 3,953,450, which issued to Bouillon et al. on Apr. 27, 1976, (aluminum); U.S. Pat. No. 2,809,971, which issued to Bernstein et al. on Oct. 15, 1957, (manganese, nickel, ferric, ferrous, cupric, zinc, and many other heavy metal salts); and U.S. Pat. No. 4,209,506, which issued to Bouillon et al. on June 24, 1980, (aluminum). All of these U.S. patents are incorporated herein by reference in their entireties.

In practicing the process of the present invention, ruminant animals such as cows may be treated with an effective bovine mastitis treating amount of at least one metallic salt of pyridine-2-thione-N-oxide, preferably the zinc or sodium salt. It is to be understood that the term "an effective amount to treat or prevent bovine mastitis" as used in the specification and claims herein is intended to include any amount or concentration of the above-noted active compounds that will treat or prevent bovine mastitis in such animals. Of course, this amount may be changed in response to numerous variables, such as the degree of effectiveness required, whether animal is milking or dry, and type of carrier, if any.

For most uses, an effective amount to treat or prevent bovine mastitis would be advantageously performed by administering from 1 to about 4 doses comprising from about 25 to about 1000 mg. of the active compound or compounds in intervals from about 12 to about 48 hours into each teat of the animal. Preferably, said doses comprise from about 25 to 100 mg. of zinc or sodium pyridine-2-thione-N-oxide per dose and said doses are administered about each 12 to 24 hours. Furthermore, the active compound or compounds used in the present process may be combined with other known veterinary and pharmaceutical agents for further benefits.

While the process of the present invention is applicable to the teats of all bovine types of mammals, the major economic impact of bovine mastitis is in connection with dairy cows. Accordingly, the following description of the invention will be concerned mainly with cows; however, it is to be understood that this invention is contemplated with the treatment of all non-human types of mammals.

This step of administering zinc pyridine-2-thione-N-oxide to the animal is preferably accomplished in the form of a composition by way of an intramammary infusion; i.e. the composition is injected into the teat through the milk canal. Such compositions would comprise at least one active compound and at least one vehicle or carrier suitable for administration in a bovine udder.

Another preferred way of administering the active compound is by applying it in a teat dip or the like wherein the outside of the teat is covered with an effective amount of the active compound to treat or prevent bovine mastitis.

Sometimes a cow or other ruminant should be treated, as a preventive manner, even if it is not clear whether she suffers from mastitis (i.e. it might be that her udder is healthy). This is important, for instance, in case that it is clear that some animals of a herd are suffering from bovine mastitis and then one may want to treat all animals of said herd in order to ascertain that no further animals would be infected. Thus, prevention as well as treatment of this disease is contemplated within the scope of the invention.

Moreover, it should be understood that the process of the present invention may be performed with milking cows as well as dry cows. In the case of dry cows, it is desirable that the metallic salt of pyridine-2-thione-N-oxide should stay for a longer time in the udder. This can be achieved by adding a slow release base (e.g., by the employment of a mineral oil or the like with or without a gelling agent as a carrier).

If at least one metallic salt of pyridine-2-thione-N-oxide is combined with a solid or liquid vehicle or carrier before application, then any suitable methods for formulating and applying the active compound or compounds may be employed. Included in such suitable methods of application are emulsifiable liquid solutions, suspensions, creams, and ointments.

Emulsifiable liquids may be prepared by dispersing the active compound in a vegetable oil or mineral oil, such as peanut oil, corn oil, soybean oil, sesame oil and the like, and then admixing the thus formed solution with a suitable surfactant or emulsifier.

Solutions and suspensions are generally formed by dissolving or dispersing the active compound in water or a suitable aqueous solution or other solvent.

Creams and ointments are generally made the same as emulsified liquids except at least one gelling agent or the like is additionally added. Such gelling agents may be natural waxes like beeswax or aluminum fatty acid salts (e.g. stearates, palmitates and oleates).

It should be clearly understood that any of the above-noted formulations, the ingredients which may make up such formulations other than the active compound and its dosage, and means for applying these formulations may include all known and conventional substances, amounts and means, respectively, that are suitable for obtaining the desired bovine mastitis treatment or prevention result. Therefore, such process parameters are not critical to the present invention.

Besides metal salts of pyridine-2-thione-N-oxide, the present invention also contemplates the use of similar pyridine-2-thione-N-oxide compounds to treat bovine mastitis. Specifically, the present invention contemplates the use of free 2-mercaptopyridine-N-oxide and organic salts (e.g., t-butylamine salt) and adducts of 2-mercaptopyridine-N-oxide, bis(pyridine-N-oxide)disulfide and its salt adducts (e.g., alkaline earth metal salts). The present invention also contemplates the use of similar compounds which have one or more other substituents on the pyridine ring (e.g., lower alkyl groups, $NO_2$, or halogens).

The following Examples further illustrate the present invention. All parts and percentages are by weight unless explicitly stated otherwise.

EXAMPLE 1

Minimum Inhibitory Concentration (MIC) Values of Zinc Pyridine-2-thione-N-oxide Required to Inhibit Growth of Microorganisms Isolated from Mastitic Cows Bacterial isolates for these studies were obtained from the New York State Mastitis Control Program, a division of veterinary clinical services of the New York State College of Veterinary Medicine, Cornell University. Samples were from cows with clinical mastitis or from milk cows that were cultured for a routine herd survey. Mastitis pathogens were identified by the use of standard bacteriologic technique[1].

[1]Microbiological Procedures for the Diagnosis of Bovine Mastitis, Washington, D.C., National Mastitis Council, Univ. New Hampshire Press, 1969.

Concentrations inhibiting growth by 50% were determined using broth dilution test procedures[2]. Briefly 0.1 ml of cultures containing approximately $9 \times 10^6$ organisms/ml were inoculated into 10 mls of Tryptose-soy broth[3] containing either 0, 1, 10, 100, or 1000 ppm of zinc pyridine-2-thione-N-oxide. These tubes were incubated at 37° C. for 18 hours and optical densities were read at 550 nanometers. Blanks for each test level consisted of a Tryptose-soy broth tube with the same concentration of test material. Concentrations of test material inhibiting growth by 50% were computed by probit analysis[4].

[2]Ericsson, M. N. and Sherris, J. C. (1971) Antibiotic Sensitivity Testing Report of an International Collaborative Study. *Acta Pathol Microbiol. Scand.* Sect. B., Suppl. 217.
[3]Diffico Manual of Dehydrated Culture Media and Reagents for Microbiological and Clinical Lab Procedures. 9th Edition, Diffico Labs, Inc., Detroit, MI (1977).
[4]Finney, D. J. (1971) Probit Analysis, Cambridge Univ. Press.

The minimum inhibitory concentration of zinc pyridine-2-thione-N-oxide for various microorganisms in broth are given in Table 1.

TABLE 1

| Organism | No. of Isolates | 50% by Weight Growth Inhibited | 100% by Weight Growth Inhibited |
|---|---|---|---|
| Staphylococcus aureus | 5 | <1.0 ppm | 5-10 ppm |
| Escherichia coli | 5 | 2.5 ± 0.5 | 13-20 |
| Pseudomonas aeruginosa | 2 | 9.6 ± 6.4 | 80-100 |
| Klebsiella pneumoniae | 3 | 2.1 ± 0.3 | 10-20 |
| Yeast Group | 5 | <1.0 | 3-6 |

These results indicate that zinc pyridine-2-thione-N-oxide is effective against microorganisms which cause bovine mastitis. They also indicate that this active compound is especially effective against E. coli and K. pneumoniae, which cause very severe forms of mastitis that could kill diseased cattle.

EXAMPLE 1A

Minimum Inhibitory Concentration (MIC) Values of Sodium Pyridine-2-thione-N-oxide Required to Inhibit Growth of Microorganisms Isolated from Mastic Cows The test procedure of Example 1 was repeated except sodium pyridine-2-thione-N-oxide was used as the active compound. The MIC of sodium pyridine-2-thione-N-oxide for various microorganisms in broth are given in Table 1A.

TABLE 1A

| Organism | No. of Isolates | 50% by Weight Growth Inhibited |
|---|---|---|
| Staphylococcus aureus | 5 | <1.0 |
| Escherichia coli | 5 | 3.4 ± 0.8 |
| Pseudomonas aeruginosa | 2 | 38.0 ± 5.2 |
| Klebsiella pneumoniae | 3 | 5.2 ± 0.8 |
| Yeast Group | 5 | <1.0 |

These results indicate that sodium pyridine-2-thione-N-oxide is also effective against microorganisms which cause bovine mastitis.

EXAMPLE 2

Minimum Inhibitory Concentrations (MIC) of Zinc Pyridine-2-thione-N-oxide Against Escherichia Coli and Staphylococcus Aureus in Milk Cultures of E. coli and S. aureus were isolated from mammary glands of cows with mastitis. Cultures were streaked on blood agar plates and incubated for 24 hours at 37° C. Colonies from these plates were inoculated into nutrient broth tubes and incubated at 37° C. overnight. One-tenth milliliter aliquots of these cultures were inoculated into 10 milliliter tubes of sterile, homogenized, skim milk containing various concentrations of zinc pyridine-2-thione-N-oxide. The concentrations of this active compound ranged from 0.01 ppm to 100 ppm and were made by serially diluting a 1% by weight aqueous suspension of zinc pyridine-2-thione-N-oxide in 10 milliliter portions of sterile skim milk.

The milk tubes containing bacteria and zinc pyridine-2-thione-N-oxide were incubated in a shaking water bath at 37° C. for 4 hours; at the end of the incubation period, 0.1 ml of the milk incubate was added to 2 ml of soft agar (0.75% by weight agar and the rest being water) and plated on blood agar plates. These plates were incubated at 37° C. for 18 hours and the microorganisms present on each plate were counted with an NBS Automatic Colony Counter. The MIC against E. coli and S. aureus were determined from the count data and are shown in Table 2.

TABLE 2

| Organism | MIC at % Inhibition of Growth | |
|---|---|---|
|  | 95% | 100% |
| E. coli | 10 ppm | 100 ppm |
| S. aureus | 10 ppm | 100 ppm |

EXAMPLES 3 AND 4

To assess the excretion and physiologic effects of zinc pyridine-2-thione-N-oxide when administered into the udder of normal, lactating cows, two cows received two doses of a 10 milliliter aqueous suspension containing either 1% or 2% by weight zinc pyridine-2-thione-N-oxide (100 mg or 200 mg of active compound) in 3 of the 4 mammary quarters of the udders. A vehicle control was infused into the 4th quarter. The two doses were given 12 hours apart.

Both the 1% and 2% suspension of zinc pyridine-2-thione-N-oxide caused an increase in California Mastitis Test (CMT)[1] scores 12 hours after the first dose (see Tables 3 and 4 for results). All quarters, including controls, responded with increased CMT scores. Normal values were observed 504 hours after the first dose; however, biopsies performed at 96 hours may have increased the time necessary to return to pre-dose levels.

[1]This well-known test is described in Bovine Mastitis by O. W. Schalm, E. J. Carroll and N. C. Jain, Lea & Febiger Publishers, Philadelphia (1971) pages 136-140.

TABLE 3

California Mastitis Test for 1% Suspension of Zinc Pyridine-2-Thione-N—Oxide

| Time | Mammary Quarter | | | |
|---|---|---|---|---|
|  | 1[a] | 2[b] | 3[b] | 4[b] |
| −12 hours | +1 | +1 | +1 | +1 |
| 0 hours | +1 | +1 | +2 | +1 |
| 12 hours | +3 | +3 | +3 | +3 |
| 24 hours | +3 | +3 | +3 | +3 |
| 36 hours | +3 | +3 | +3 | +3 |
| 48 hours | +3 | +3 | +3 | +3 |
| 72 hours | +3 | +3 | +3 | +3 |
| 96 hours | +2 | +2 | +2 | +2 |
| 168 hours | +3 | +3 | +3 | +3 |
| 504 hours | +2 | +1 | +2 | +1 |

[a]Control quarter (vehicle control)
[b]Quarter receiving 10 ml of 1% suspension of active compound at 0 hour and 12 hours

TABLE 4

California Mastitis Test for 2% Suspension of Zinc Pyridine-2-Thione-N—Oxide

| Time | Mammary Quarter | | | |
|---|---|---|---|---|
|  | 1[a] | 2[b] | 3[b] | 4[b] |
| −12 hours | Tr | Tr | Tr | Tr |
| 0 hours | Tr | Tr | Tr | Tr |
| 12 hours | +3 | +3 | +3 | +3 |
| 24 hours | +2 | +3 | +2 | — |
| 36 hours | +3 | +3 | +3 | — |
| 48 hours | +3 | +3 | +3 | +3 |
| 60 hours | +2 | +2 | +3 | +3 |
| 72 hours | +2 | +2 | +3 | +3 |
| 96 hours | +1 | +1 | +1 | +2 |
| 168 hours | +2 | +3 | +3 | +3 |

TABLE 4-continued

California Mastitis Test for 2% Suspension
of Zinc Pyridine-2-Thione-N—Oxide

| Time | Mammary Quarter | | | |
|---|---|---|---|---|
|  | 1[a] | 2[b] | 3[b] | 4[b] |
| 504 hours | Tr | Tr | Tr | Tr |

[a]Control quarter (vehicle control)
[b]Quarter receiving 10 ml of 2% suspension of active compound at 0 hour and 12 hours The California Mastitis Test is scored from best to worst in the following way:
N=negative
Tr=trace
1=weak
2=distinct positive
3=strong positive Accordingly, the above scores and other observations indicate that the administration into a normal lactating bovine mammary gland of two doses of 10 ml of a 1% zinc pyridine-2-thione-N-oxide suspension increased sensitivity of the udder to palpation, produced flakes and clots in milk, increased CTM scores, and depressed milk output. However, no evidence of an inflammatory response was observed 96 hours past initial dose. Also, no systemic effects were noted.

Furthermore, the effects of the two doses of the 10 ml of 2% zinc pyridine-2-thione-N-oxide were in general similar to 1% infusion except with increased severity. The udder became extremely sensitive to palpation and felt warm. Milk production was reduced more dramatically than the 1% infusion, and evidence of an inflammatory response was present 96 hours after the initial dose.

EXAMPLES 5 AND 6

Because the above-noted results of the two 10 ml doses of 1% and 2% infusions of zinc pyridine-2-thione-N-oxide indicated that such large doses had some adverse effects on cow's udder, smaller dosages were investigated with the California Mastitis Test. Specifically, one healthy, lactating cow was used to determine the effect of two smaller concentrations of zinc pyridine-2-thione-N-oxide.

First, ten milliliters of a 0.25% suspension of this active compound (2.5 mg) in peanut oil were infused into each quarter after a milking. Two more 10 ml infusions of the same concentration were later infused at 12 hour intervals. The results of this test are given in Table 5.

After a period of 36 hours had passed, the same cow was administered with 3 doses of 10 ml of peanut oil containing 0.50% by weight of zinc pyridine-2-thione-N-oxide (50 mg). The 3 doses were given at 12 hour intervals. The results of this test are given in Table 6.

TABLE 5

California Mastitis Test With Three Infusions
of 10 ml of Peanut Oil Containing
0.25% Zinc Pyridine-2-Thione-N—Oxide

| Time | Quarter | | | |
|---|---|---|---|---|
|  | 1 | 2 | 3 | 4 |
| −12 hours | N | N | N | N |
| 0 hours | N | N | N | N |
| 12 hours | Tr | Tr | Tr | Tr |
| 24 hours | Tr | Tr | Tr | Tr |
| 36 hours | N | Tr | N | Tr |
| 48 hours | N | Tr | N | Tr |
| 72 hours | N | Tr | N | N |
| 96 hours | Tr | N | N | Tr |
| 168 hours | Tr | Tr | N | N |

TABLE 6

California Mastitis Test With Three Infusions
of 10 ml of Peanut Oil Containing
0.50% Zinc Pyridine-2-Thione-N—Oxide

| Time | Quarter | | | |
|---|---|---|---|---|
|  | 1 | 2 | 3 | 4 |
| −12 hours | N | Tr | N | N |
| 0 hours | N | Tr | N | N |
| 12 hours | N | Tr | Tr | N |
| 24 hours | Tr | N | N | Tr |
| 36 hours | Tr | Tr | Tr | 1 |
| 48 hours | 1 | 1 | 2 | 1 |
| 72 hours | 1 | 1 | 2 | 1 |
| 96 hours | 1 | 2 | 1 | 1 |
| 168 hours | Tr | 1 | 1 | Tr |

The three doses for each test were given at 0 hours, 12 hours, and 24 hours. No control quarter was used in these tests. The same CMT scoring system as mentioned in Examples 3 and 4 was used here.

As can be seen from Tables 5 and 6, the 0.25% zinc pyridine-2-thione-N-oxide suspension had no effect on CMT scores or on other physical observations. Administration of 0.50% zinc pyridine-2-thione-N-oxide resulted in a very slight rise in CMT scores starting 12 hours after the third dose and continued through the end of the observation period. In this latter test, an increased firmness of the udder to palpation was also observed.

EXAMPLES 7 AND 8

Milk samples produced in Examples 3 and 4 were analyzed for any residual zinc pyridine-2-thione-N-oxide content. The analyses were performed by differential pulse polarography technique using a Princeton Applied Research (PAR) Model 174A Polarographic Analyzer equipped with a Model 172A Drop Timer and a 10 ml cell. The results of this residual testing are given in Tables 7 and 8 (amounts in ppm stand for the parts of zinc pyridine-2-thione-N-oxide per million parts of milk by weight).

TABLE 7

Residual Content of Zinc Pyridine-2-
Thione-N—Oxide In Milk After Two Doses of
10 ml Aqueous Suspensions of 1% Active Compound

| Time | Mammary Quarter | | | |
|---|---|---|---|---|
|  | 1[a] | 2[b] | 3[b] | 4[b] |
| −12 hours | ND[1] | ND | ND | ND |
| 12 hours | ND | ND | ND | ND |
| 24 hours | ND | 0.2 ppm | <0.2 ppm | 0.3 ppm |
| 72 hours | <0.2 ppm | <0.2 | <0.2 | <0.2 |
| 96 hours | <0.2 | <0.2 | <0.2 | <0.2 |

TABLE 8

Residual Content of Zinc Pyridine-2-Thione-N—Oxide In Milk After Two Doses of 10 ml Aqueous Suspension of 2% Active compound

| Time | Mammary Quarter | | | |
|---|---|---|---|---|
| | 1[a] | 2[b] | 3[b] | 4[b] |
| −12 hours | ND | ND | ND | ND |
| 12 hours | ND | ND | ND | ND |
| 24 hours | 0.2 ppm | ND | ND | — |
| 72 hours | ND | ND | 4[2] | ND |
| 96 hours | ND | 0.2 ppm | 0.2 ppm | 0.2 ppm |

[a] control quarter
[b] quarter infused with 1% zinc pyridine-2-thione-N—oxide suspensions in two doses at 0 and 12 hours
[1] Not detected, less than 0.1 ppm of active compound
[2] This 3rd quarter sample was the only sample analyzed which gave a high level. The reasons for this result seem inconsistent with other values Samples not analyzed for residual values were those taken at 0 hours, 36 hours, 48 hours, 168 hours, and 504 hours.

The results of this residual testing indicate that very low levels of zinc pyridine-2-thione-N-oxide were found in milk after infusion of aqueous suspensions containing either 1% or 2% by weight of the active compound. If lower amounts of the active compound were infused (e.g., in 0.5% or 0.25% suspenions) the residual amounts may be expected to be lower.

The above results, namely the good microbiological activity in milk, the relative quick disappearance from the milk, and the low irritation caused to the udder at low concentrations and its relative non-toxicity ($LD_{50}$ rats=200 mg/Kg) indicate that zinc pyridine-2-thione-N-oxide would be suitable to be used in the treatment of bovine mastitis.

What is claimed is:

1. A method of treating an animal for bovine mastitis which comprises administering to said animal an effective amount of at least one metallic salt of pyridine-2-thione-N-oxide to treat or prevent bovine mastitis.

2. The method of claim 1 wherein the administration is effected to the teats and udder of a cow.

3. The method of claim 2 wherein from 1 to about 4 doses of about 25 to about 1000 milligrams of zinc pyridine-2-thione-N-oxide are infused into each teat of said cow at intervals of 12 to 48 hours.

4. The method of claim 3 wherein from about 25 to about 100 mg. of said zinc pyridine-2-thione-N-oxide are infused into each teat of said cow.

5. The method of claim 2 wherein an effective amount of zinc pyridine-2-thione-N-oxide is applied to the outside of the teats and udder of a cow.

6. The method of claim 2 wherein from 1 to about 4 doses of about 25 to about 1000 milligrams of sodium pyridine-2-thione-N-oxide are infused into each teat of said cow.

7. The method of claim 6 wherein from about 25 to about 100 mg. of said sodium pyridine-2-thione-N-oxide are infused into each teat of said cow.

8. The method of claim 2 wherein an effective amount of sodium pyridine-2-thione-N-oxide is applied to the outside of the teats and udder of a cow.

* * * * *